United States Patent
Sato et al.

(10) Patent No.: US 8,864,308 B2
(45) Date of Patent: Oct. 21, 2014

(54) IMAGING APPARATUS AND IMAGING METHOD

(75) Inventors: Makoto Sato, Tokyo (JP); Mitsuro Sugita, Vienna (AT)

(73) Assignee: Canon Kabushiki Kaisha, Tokyo (JP)

( * ) Notice: Subject to any disclaimer, the term of this patent is extended or adjusted under 35 U.S.C. 154(b) by 387 days.

(21) Appl. No.: 13/266,285

(22) PCT Filed: May 20, 2010

(86) PCT No.: PCT/JP2010/058944
§ 371 (c)(1),
(2), (4) Date: Oct. 26, 2011

(87) PCT Pub. No.: WO2010/134641
PCT Pub. Date: Nov. 25, 2010

(65) Prior Publication Data
US 2012/0044457 A1 Feb. 23, 2012

(30) Foreign Application Priority Data

May 22, 2009 (JP) ................. 2009-123908
Mar. 24, 2010 (JP) ................. 2010-068281

(51) Int. Cl.
| | |
|---|---|
| A61B 3/14 | (2006.01) |
| A61B 3/12 | (2006.01) |
| A61B 3/10 | (2006.01) |
| A61B 5/00 | (2006.01) |
| G01N 21/47 | (2006.01) |
| G01B 9/02 | (2006.01) |

(52) U.S. Cl.
CPC ... *A61B 3/12* (2013.01); *A61B 3/14* (2013.01); *A61B 3/1025* (2013.01); *A61B 3/1005* (2013.01); *A61B 3/102* (2013.01); *A61B 5/0066* (2013.01); *A61B 5/0073* (2013.01); *G01N 21/4795* (2013.01); *G01B 9/02028* (2013.01); *G01B 9/02091* (2013.01); *G01B 9/02048* (2013.01); *G01B 2290/65* (2013.01)
USPC ................... 351/206; 351/205; 351/246

(58) Field of Classification Search
CPC .... A61B 3/0058; A61B 3/0075; A61B 3/102; A61B 3/10; A61B 3/1015; A61B 3/1025; A61B 3/14
USPC .......... 351/205, 206, 210, 221, 246
See application file for complete search history.

(56) References Cited

U.S. PATENT DOCUMENTS

| | | |
|---|---|---|
| 4,298,283 A | 11/1981 | Makosch et al. |
| 5,321,501 A | 6/1994 | Swanson et al. |

(Continued)

FOREIGN PATENT DOCUMENTS

| | | |
|---|---|---|
| JP | 2004-105708 A | 4/2004 |
| JP | 2008-508068 A | 3/2008 |

OTHER PUBLICATIONS

Jorgensen T.M. et al., "Enhancing the signal-to-noise ratio in ophthalmic optical coherence tomography by image registration-method and clinical examples," Journal of Biomedical Optics, 12(4), 041208, Jul./Aug. 2007.

(Continued)

*Primary Examiner* — Huy K Mai
(74) *Attorney, Agent, or Firm* — Fitzpatrick, Cella, Harper & Scinto

(57) ABSTRACT

An imaging apparatus includes changing unit for changing a positional relation of irradiation positions of a plurality of measuring beams to be radiated onto an object. The imaging apparatus includes scanning unit for scanning the plurality of measuring beams in the positional relation which has been changed by the changing unit, and acquiring unit for acquiring an optical coherence tomographic image of the object on the basis of the plurality of measuring beams.

27 Claims, 13 Drawing Sheets

(56) References Cited

U.S. PATENT DOCUMENTS

| | | | |
|---|---|---|---|
| 5,459,570 | A | 10/1995 | Swanson et al. |
| 7,695,140 | B2 | 4/2010 | Fercher |
| 8,425,036 | B2 * | 4/2013 | Yoshida et al. ............... 351/205 |
| 2007/0219437 | A1 | 9/2007 | Schurman et al. |
| 2008/0284981 | A1 | 11/2008 | Fercher |
| 2010/0166293 | A1 | 7/2010 | Sugita et al. |
| 2010/0181462 | A1 | 7/2010 | Sugita |
| 2011/0096333 | A1 | 4/2011 | Suehira et al. |
| 2011/0098560 | A1 | 4/2011 | Suehira et al. |
| 2011/0249236 | A1 | 10/2011 | Saito et al. |
| 2012/0053904 | A1 | 3/2012 | Yuasa et al. |
| 2012/0075640 | A1 | 3/2012 | Sakagawa et al. |

OTHER PUBLICATIONS

Sticker M. et al., "Quantitative Differential Phase Measurement and Imaging in Transparent and Turbid Media by Optical Coherence Tomography", Optics Letters, OSA, Optical Society of America, Washington, DC, US, vol. 26, No. 8, Apr. 15, 2001, pp. 518-520.

International Search Report and Written Opinion of the International Searching Authority mailed Aug. 26, 2010 in International Application No. PCT/JP2010/058944.

Notification Concerning Transmittal of International Preliminary Report on Patentability mailed Dec. 1, 2011, an International Preliminary Report on Patentability dated Nov. 22, 2011, and a Written Opinion of the International Searching Authority, in PCT/JP2010/058944.

Dec. 18, 2013 Chinese Official Action in Chinese Patent Appln. No. 201080022515.1.

* cited by examiner

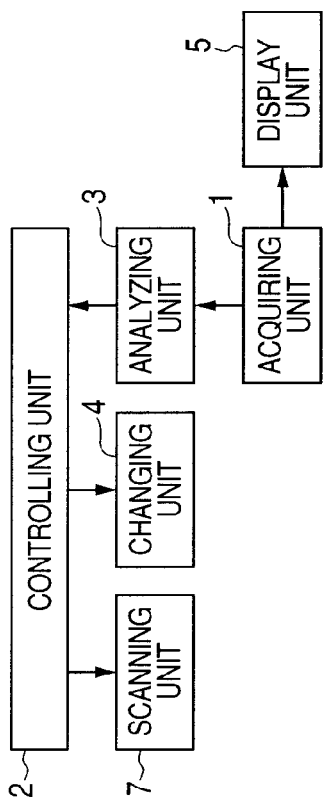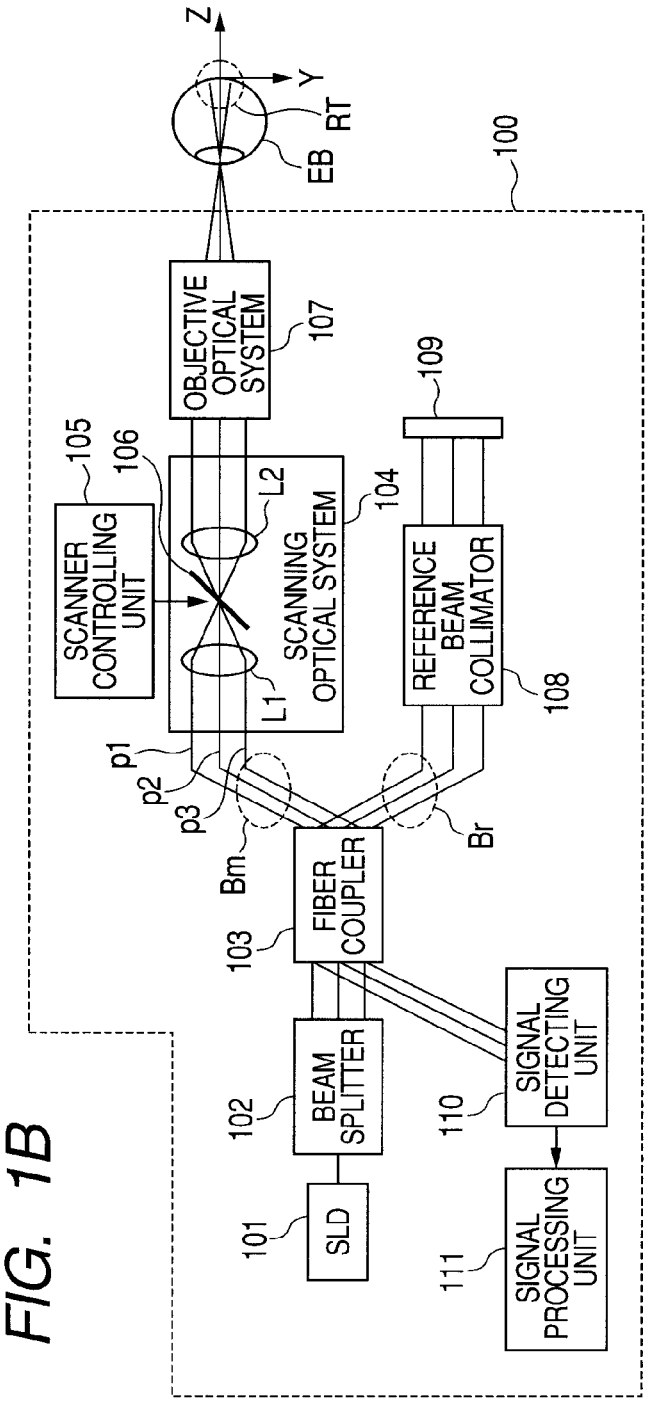

FIG. 8A
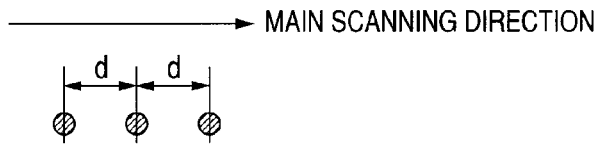
FIG. 8B
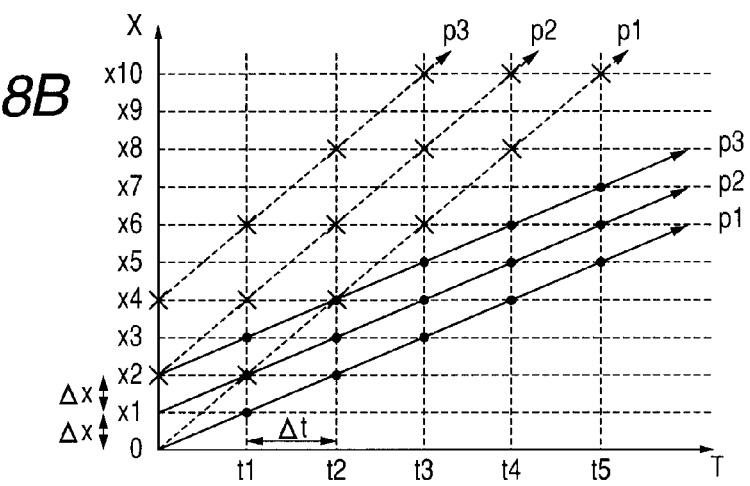
FIG. 8C
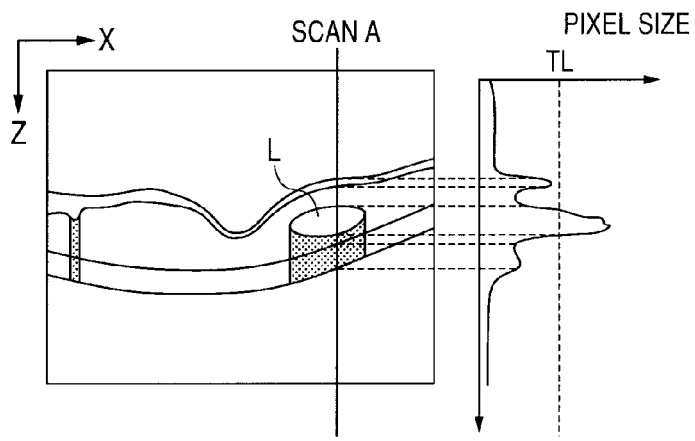
FIG. 8D
| PATIENT INFORMATION | EXISTENCE OF ABNORMAL STRUCTURE | TOMOGRAPHIC IMAGE DATA |
|---|---|---|

IMAGING APPARATUS AND IMAGING METHOD

TECHNICAL FIELD

The present invention relates to an imaging apparatus and an imaging method for imaging an object by using an optical coherence tomography, and more particularly to a radiation method of a measuring beam.

BACKGROUND ART

In recent years, an imaging apparatus (hereinafter also referred to as OCT apparatus) for imaging an object by the use of an optical coherence tomography (OCT) using interference by a low coherence light has been used in a medical field, especially in an ophthalmologic field. Because the OCT apparatus uses a characteristic of light, the OCT apparatus can acquire a tomographic image at the high resolution of about a micrometer, which is the order of a wavelength of light. When an eye to be inspected, such as a fundus, is measured here, the examinee sometimes moves, blinks, or randomly joggles (flicks) during measurement. There is a problem, consequently, that a tomographic image of an eye to be inspected, which has been acquired with an OCT apparatus, is distorted.

In order to solve the problem, Thomas M. Jorgensen et al., "Enhancing the signal-to-noise ratio in ophthalmic optical coherence tomography by image registration-method and clinical examples," Journal of Biomedical Optics, 12(4), 041208, July/August, 2007 discloses acquiring tomographic images at the same position of an object a plurality of times, aligning those tomographic images to one another, and then averaging the tomographic images to acquire one tomographic image. The method, thereby, enables the acquisition of a tomographic image having a high S/N ratio and a high image quality. At this time, there is the possibility that displacement between the position of the tomographic image acquired first and that of the tomographic image acquired last becomes large during acquiring the tomographic images a plurality of times. It will be appreciated that this makes it difficult to align the tomographic images and that the displacement makes it impossible to improve the image quality of the tomographic images as a result, even if the averaging is performed. For this reason, it can be said that it is preferable to perform imaging speedily from the point of view of making a tomographic image have high image quality at the time of imaging an eye to be inspected.

Furthermore, Published Japanese Translation of a PCT Application No. 2008-508068 discloses the OCT radiating a plurality of points of lights to a pupil in order to acquire the three-dimensional structure of the pupil.

DISCLOSURE OF THE INVENTION

An OCT apparatus radiating a plurality of lights to an eye to be inspected can image the eye to be inspected at higher speed than that of an OCT apparatus radiating a single light to the eye to be inspected. At this time, it is desirable to configure the OCT apparatus radiating the plurality of lights to the eye to be inspected in such a way that either the speed of imaging or the quality of imaging can have priority to the other according to an imaging region of the object, such as the eye to be inspected.

An imaging apparatus according to the present invention comprises:
  a radiating unit for radiating a plurality of measuring beams to an object;
  a changing unit for changing a positional relation among irradiation positions of the plurality of measuring beams radiated at a predetermined same layer of the object by the radiating unit;
  a scanning unit for scanning the plurality of measuring beams in the positional relation changed by the changing unit; and
  an acquiring unit for acquiring an optical coherence tomographic image of the object based on the plurality of measuring beams used for the scanning by the scanning unit.

Furthermore, the imaging apparatus according to another of the present invention comprises:
  a radiating unit for radiating a plurality of measuring beams to an object;
  a changing unit for changing a positional relation among irradiation positions of the plurality of measuring beams radiated to the object by the radiating unit;
  a scanning unit for scanning the plurality of measuring beams in the positional relation changed by the changing unit;
  an acquiring unit for acquiring an optical coherence tomographic image of the object based on the plurality of measuring beams used by the scanning by the scanning unit;
  an analyzing unit for analyzing a wide area image of the object acquired in a scanning region wider than that of acquiring the optical coherence tomographic image; and
  a controlling unit for controlling the changing unit by using an analysis result of the analyzing unit.

Furthermore, an imaging apparatus according to another present invention comprises:
  a radiating unit for radiating a plurality of measuring beams to an object;
  a scanning unit for aligning irradiation positions of the plurality of measuring beams, radiated onto a predetermined same layer of the object by the radiating unit, almost in a main scanning direction to scan the plurality of measuring beams;
  a changing unit for changing scanning speeds of the plurality of measuring beams in the main scanning direction; and
  an acquiring unit for acquiring an optical coherence tomographic image of the object based on the plurality of measuring beams used for the scanning by the scanning unit.

Furthermore, an imaging method according to the present invention comprises the steps of:
  radiating a plurality of measuring beams to an object;
  scanning the plurality of measuring beams;
  acquiring an optical coherence tomographic image of the object based on the plurality of measuring beams;
  analyzing a wide area image of the object in a scanning region wider than that of acquiring the optical coherence tomographic image; and
  changing a positional relation among irradiation positions of the plurality of measuring beams radiated to the object by using an analysis result of the step of analyzing.

An OCT apparatus according to the present invention can change the positional relation among the irradiation positions of a plurality of measuring beams radiated to the object, such as an eye to be inspected. As a result, the OCT apparatus can be configured to give high priority to either the high-speed performance or the high image quality performance of imaging especially according to the imaging region of an object.

BRIEF DESCRIPTION OF THE DRAWINGS

FIGS. 1A, 1B, and 1C are diagrams for illustrating the configuration of an imaging apparatus in a first embodiment of the present invention.

FIGS. 8A, 8B, 8C, and 8D are diagrams for illustrating the configuration of the imaging apparatus of each embodiment of the present invention.

BEST MODE FOR CARRYING OUT THE INVENTION

Figure 1C:
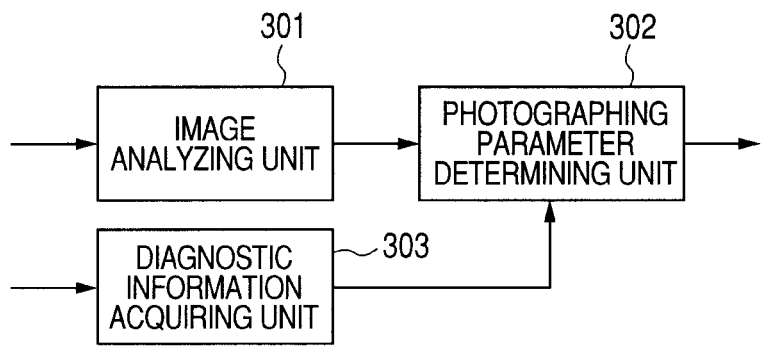

In the following, imaging apparatus according to embodiments will be described in detail with reference to the accompanying drawings.

In addition, an imaging apparatus (or also referred to as an imaging apparatus for imaging an optical coherence tomographic image of an object by radiating a plurality of measuring beams to the object) according to the present invention has the feature of changing the positional relation among irradiation positions of the plurality of measuring beams radiated to the object, such as an eye to be inspected (particularly to a predetermined same layer, such as a fundus surface of the eye to be inspected). It is hereby possible to configure the imaging apparatus to be able to give priority to either the high-speed performance of imaging or the high image quality thereof according to an imaging region of the eye to be inspected.

The imaging apparatus (OCT apparatus 100) according to the present invention includes a changing unit (changing unit 4) for changing the positional relation, scanning unit (scanning unit 7) for performing scanning with a plurality of measuring beams in the changed positional relation, and acquiring unit (acquiring unit 1) for acquiring an optical coherence tomographic image of an object based on the plurality of measuring beams here.

At this time, the changing unit (changing unit 4) is preferably means for changing intervals between a plurality of irradiation positions. This means that the densities of the plurality of irradiation positions can simply be changed. It is, hereby, possible to increase or decrease the number of times (number of times of irradiation) per unit time of irradiation to the scanning region by the scanning unit (scanning unit 7). For example, by changing the positional relation so as to increase the number of times (for example, by arranging the irradiation positions almost in the main scanning direction of the scanning unit (scanning unit 7)) to the watching region (such as a macula or an optic disc) useful for diagnosis, a tomographic image having a high image quality in the watching region can be imaged. In addition, the number of times may be increased to an imaging region having a bad S/N ratio as a result of the analysis of the acquired tomographic image with the analyzing unit.

Furthermore, the changing unit (changing unit 4) preferably changes the width of the scanning unit (scanning unit 7) in the sub scanning direction in the plurality of irradiation positions. This can be realized by, for example, changing the arrangement of the plurality of irradiation positions from the main scanning direction of the scanning unit (scanning unit 7) to the sub scanning direction thereof or from the sub scanning direction to the main scanning direction with the changing unit (changing unit 4).

Furthermore, because the plurality of measuring beams is radiated to the eye to be inspected, the averaging of the respective tomographic images imaged at the same place would enable the acquisition of a tomographic image having a high image quality. In the case of an OCT apparatus radiating a single measuring beam, it is needed to perform imaging a plurality of times or to perform imaging by enlarging the light quantity per light in order to acquire a tomographic image having a high image quality, and consequently the case becomes a burden for an examinee.

First Embodiment

An imaging apparatus of the present embodiment is configured to measure an object, particularly a fundus (retina). In particular, in order to acquire a tomographic image effective for the diagnosis of glaucoma, a watching region is determined on the basis of a result of the acquisition of a first tomographic image. Then, in order to acquire a tomographic image having higher image quality in the watching region, the positional relation (the arrangement of a plurality of irradiation positions) of the plurality of irradiation positions acquired by radiating a plurality of measuring beams to the fundus could be changed.

First, the OCT apparatus according to the present embodiment is described with reference to FIG. 1A, a block diagram, and FIG. 1B, a schematic view for describing the configuration of the OCT apparatus. A tomographic image is acquired by scanning a retina part RT of an eyeball EB with a plurality of measuring beams there. An acquiring unit 1 of the present embodiment produces a tomographic image by performing the Fourier transformation of a signal detected by separating an interference light into its spectral components. This is an SD-OCT (also referred to as a spectral domain system in OCT), one of a FD-OCT (Fourier domain system in OCT). The OCT apparatus according to the present invention is, however, not restricted to this system, but it is also possible to apply an SS-OCT and a TD-OCT. Here, it is supposed that the direction perpendicular to the paper surface of FIG. 1B is set as an X-axis, and the depth direction of the eyeball EB, crossed with the X-axis at right angles, is set as Z-axis, and the direction crossed with the X-axis at right angles in the same plane as that of the Z-axis is set as a Y-axis. Then, the scanning in the X-axis direction with the measuring beams will be referred to as main scanning, and the scanning in the Y-axis direction with the measuring beams will be referred to as sub scanning. The imaging apparatus of the present embodiment is configured as an imaging apparatus by the OCT for imaging a tomographic image of an object by using combined lights, produced by making a reference beam interfere with the respective plurality of returning lights of the plurality of measuring beams radiated to an object.

To put it concretely, as illustrated in FIG. 1B, a light emitted from an SLD 101, which is a low coherence light source, is split into three light fluxes in a beam splitter 102, and enters a fiber coupler 103. The fiber coupler 103 separates the entered light fluxes into a measuring beam flux Bm and a reference beam flux Br, and outputs the measuring beam flux Bm to a scanning optical system 104 through optical fibers and the reference beam flux Br to a reference beam collimator 108. The scanning optical system 104 (also referred to as the scanning unit 7) condenses the input measuring beam flux Bm to a galvanometer mirror 106, and performs the scanning with the measuring beams.

Figure 2A:
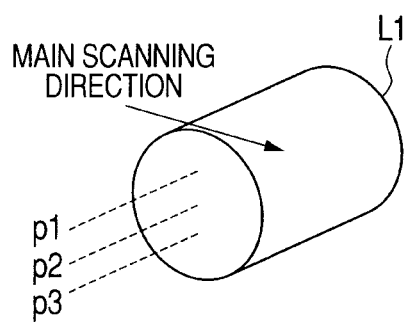
FIGS. 2A, 2B, 2C, and 2D are views for illustrating arrangements of measuring beams in the first embodiment of the present invention.
Figure 2B:
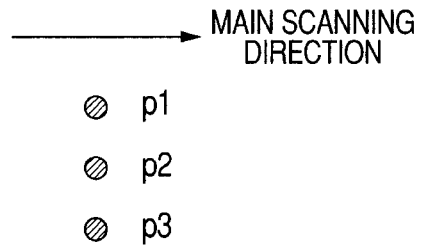
Figure 2C:
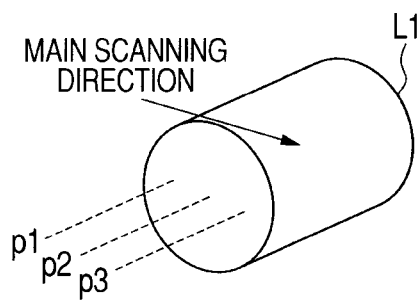
Figure 2D:
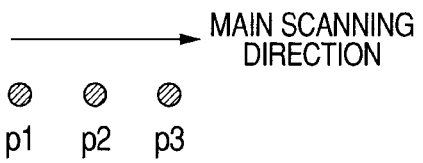

FIGS. 2A to 2D illustrate the arrangement of the irradiation positions of measuring beams in the scanning optical system 104, and FIG. 2A illustrates the case of making three measuring beams p1, p2, and p3 constituting the measuring beam flux Bm enter almost perpendicular to the main scanning direction (sub scanning direction). On the other hand, FIG. 2C illustrates the case of making the three measuring beams p1, p2, and p3 enter almost horizontally. Furthermore, FIGS. 2B and 2D illustrate the arrangements of the respective measuring beams to the main scanning direction on the retina RT. In FIG. 2B, the measuring beams p1, p2, and p3 are arranged perpendicularly to the main scanning direction, and in FIG. 2D, the measuring beams p1, p2, and p3 are horizontally arranged. At this time, the changing unit 4 changes the arrangement of the plurality of irradiation positions of the scanning unit 7 from the main scanning direction to the sub scanning direction or from the sub scanning direction to the main scanning direction.

The galvanometer mirror 106 can be driven into two axes, and a scanner controlling unit 105 performs the drive control of the mirror so as to scan the retina RT with the measuring beams into the main scanning direction and the sub scanning direction. The measuring beam flux Bm, used for the scanning, arrives at the retina RT, which is the object to be measured, through an objective optical system 107, and is reflected to arrive at the fiber coupler 103 again through the objective optical system 107 and the scanning optical system 104 there.

On the other hand, the reference beam flux Br, output from the fiber coupler 103, is reflected by a reference mirror 109 through the optical fibers and the reference beam collimator 108, and again arrives at the fiber coupler 103. The reference beam flux Br interferes with the measuring beam flux Bm to produce an interference light there, and the produced interference light is input into a signal detecting unit 110.

That is, three measuring beams interfere with the reference beam flux Br, and then three interference lights are led to be input into the signal detecting unit 110. The signal detecting unit 110 detects each interference light to output the detected interference lights as three electrical interference signals to a signal processing unit 111. The signal processing unit 111 produces three signals (hereinafter referred to as scans A) from the respective interference signals corresponding to the reflectances of the retina RT along the Z-axis direction by the signal processing, such as Fourier transformation, and outputs the produced three signals.

Figure 4A:
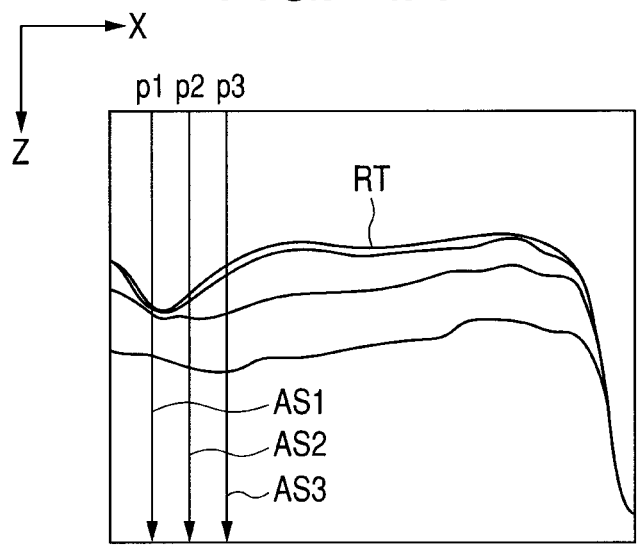
FIGS. 4A and 4B are diagrams for illustrating the acquisition of a tomographic image of a horizontal arrangement in the first embodiment of the present invention.
Figure 4B:
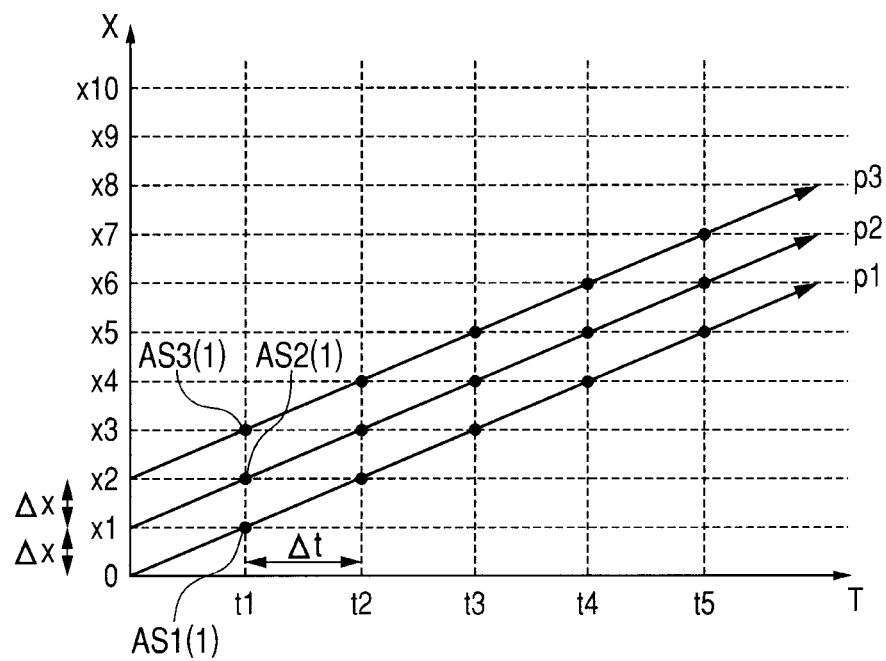

FIGS. 4A and 4B illustrate the three scans A AS1, AS2, and AS3 in the horizontal arrangement illustrated in FIGS. 2C and 2D together with the retina RT.

As described above, the imaging apparatus according to the present embodiment includes the changing unit 4, changing the positional relation (arrangement) of the plurality of irradiation positions on the retina RT. The imaging apparatus is, hereby, configured to perform the imaging having a high image quality by changing the incident arrangement of measuring beams in a region in which the imaging of high resolution is required. That is, as minutely described in the following, the imaging apparatus is configured so as to image a tomographic image by changing the arrangement of the measuring beams p1, p2, and p3 to the horizontal arrangement illustrated in FIG. 2D in a region in which imaging of high resolution is required, and so as to perform scanning with the measuring beams p1, p2, and p3 in the vertical arrangement illustrated in FIG. 2B in the other region.

Next, the overall operation of the imaging apparatus according to the present embodiment, performing imaging by changing the incident arrangement of the measuring beams to a retina RT, is described with reference to the flow chart illustrated in FIG. 5A.

Figure 3A:
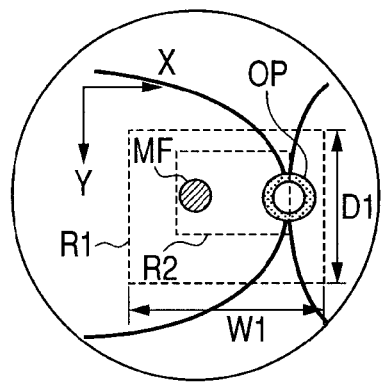
FIGS. 3A, 3B, 3C, and 3D are views for illustrating acquiring regions of a tomographic image in the first embodiment of the present invention.
Figure 3B:
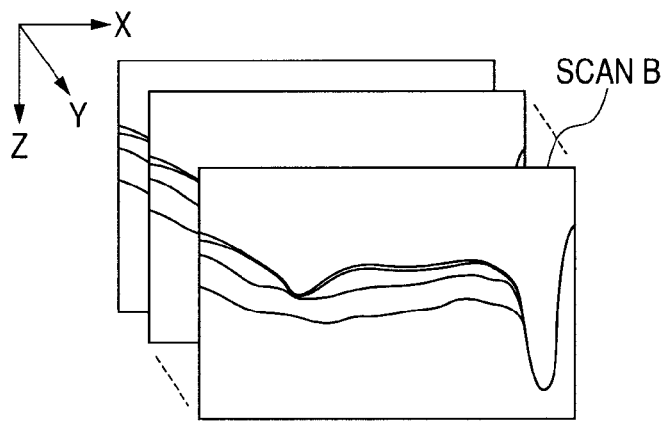
Figure 3C:
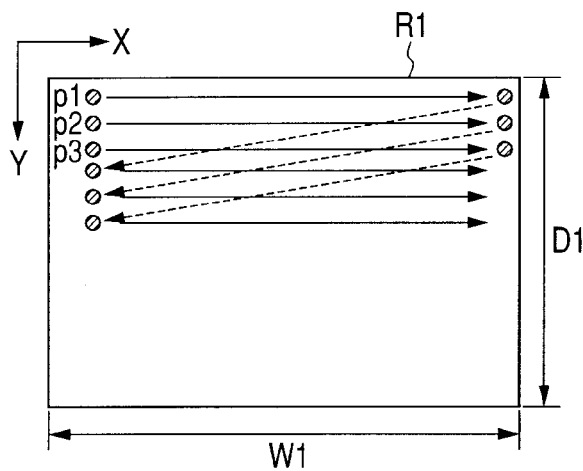
Figure 3D:
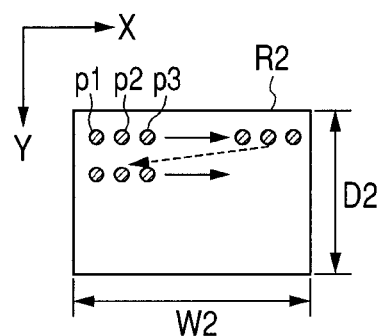

First, the imaging apparatus performs scanning with the measuring beams arranged in the vertical arrangement illustrated in FIG. 2A to acquire a tomographic image with the acquiring unit 1 in the step of S100, which is a first acquiring step of acquiring a first tomographic image. W1 and D1 in FIGS. 3A and 3C are sample numbers of tomographic images in the X-axis direction and the Y-axis direction corresponding to a measuring region R1 in a fundus. The sample numbers are set by an operator of the imaging apparatus according to the present embodiment. Furthermore, the measuring region R1 is set in a wide range (also referred to as a wide area region) including an optic disc OP and a macula MF of the fundus. In addition, an image in the measuring region R1 is also referred to as a wide area image.

In the step of S100, as illustrated in FIG. 3C, the measuring beams are used for the scanning in the vertical arrangement, and scans A by the respective measuring beams are arranged W1 scans in the X-axis direction to be a tomographic image corresponding to an X, Z-plane. If the tomographic image is supposed to be referred to as a scan B, three scans B are led to be acquired by only one time of main scanning, and the tomographic image of the measuring region R1 (wide area region) can be acquired at about three times the speed in comparison with the case of using one measuring beam. In the following description, the tomographic image acquired at the step of S100 will be referred to as a wide area tomographic image. The acquiring unit 1 outputs the wide area tomographic image acquired as above to an analyzing unit 3 and a display unit 5, and the display unit 5 stores the wide area tomographic image in a not-illustrated memory.

In the step of S200, the wide area tomographic image is analyzed as follows to determine a measuring region. The analyzing unit 3 analyzes the wide area tomographic image, acquired as above, to further specify a region important for diagnosis, and outputs the position to a controlling unit 2. That is, the analyzing unit 3 analyzes the wide area tomographic image, acquired previously as above, to determine an image range of a tomographic image important for diagnosis, which tomographic image is to be thereafter acquired. In the present embodiment, as described above, a region R2 around a part of the eye between the optic disc OP and the macula MF is determined as a region necessary for diagnosis of glaucoma as illustrated in FIG. 3A. This is because there is the necessity of minutely observing the state of the retina layer at this part in the diagnosis of glaucoma.

Figure 6A:
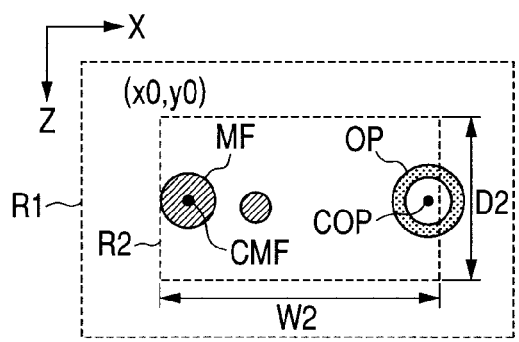
FIGS. 6A, 6B, 6C, 6D, and 6E are diagrams for illustrating the configuration of the imaging apparatus in the first embodiment of the present invention.

The analyzing unit 3, as illustrated in FIG. 6A, analyses the measuring region R1 of a wide area tomographic image to detect a COP and a CMF, corresponding to the centers of the optic disc portion OP and the macula MF, respectively, and determines the measuring region R2 having a boundary including COP and CMF with an interposed predetermined width around them. The detection method of the CMF and the COP will be described later. The analyzing unit 3 outputs the coordinates (x0, y0) of the top left corner of the measuring region R2 and the numbers of pixels W2 and D2 in the X and Y-axis directions, respectively, to the controlling unit 2.

In the step of S300, the positional relation among a plurality of irradiation positions (the arrangement of the plurality of irradiation positions) acquired by radiating a plurality of measuring beams to an object as follows is changed. First, the signals pertaining to the position and the number of pixels of the measuring region R2 are input from the analyzing unit 3 to the controlling unit 2. Next, a command (signal) to change the three irradiation positions from the vertical arrangement, illustrated in FIG. 2A, to the horizontal arrangement, illustrated in FIG. 2C, is output from the controlling unit 2 to the changing unit 4. Then, the changing unit 4 turns the three optical fibers guiding the measuring beam flux Bm by 90 degrees so as to be in the horizontal arrangement. In the present embodiment, as the changing unit 4, for example, an actuator, such as a motor and solenoid, can be used, and the turning of the optical fibers is performed by operating a not-illustrated driving mechanism. Giving clear details about it, the plurality of measuring beams is radiated from the ends of the plurality of optical fibers to the object, and the changing unit 4 is configured so as to turn the ends of the plurality of optical fibers. The turning is that around the radiation directions of the plurality of measuring beams as the turning axes.

Next, in the step of S400, which is a second acquiring step of acquiring a second tomographic image, the tomographic image is acquired as follows. The controlling unit 2 outputs the position and the number of pixels of the measuring region R2, input from the analyzing unit 3 beforehand, to the acquiring unit 1, and the acquiring unit 1 performs the measurement of the region.

FIGS. 4A and 4B illustrate the acquisition of the scans A at the time of changing the measuring beams into the horizontal arrangement. As shown in FIG. 4A, if the scans A obtained by the measuring beams p1, p2, and p3 are denoted by AS1, AS2, and AS3, respectively, then the signal detecting unit 110 performs the detection of interference lights at the timings illustrated in FIG. 4B. That is, if it is supposed that the interval between each of the measuring beams is $\Delta x$ to be an equal interval and the measuring beams move into the main scanning direction at a uniform velocity in the present embodiment, the relation among the measuring beams becomes the one illustrated in FIG. 4B. When the signal detecting unit 110 samples the interference signals at the interval of $\Delta t$ in terms of time here, then the interference signals of the respective measuring beams are led to be acquired at the timings illustrated by black dots in the same figure. Furthermore, the signal processing unit 111 processes the detected interference signals, and primarily stores the produced three scans A AS1, AS2, and AS3 in a not-illustrated memory. If the similar sampling is performed, three scan A groups illustrated in the following (formula 1) are acquired by one time main scanning.

$$AS1=\{AS1(0),AS1(1),AS1(2),\ldots\}$$

$$AS2=\{AS2(0),AS2(1),AS2(2),\ldots\}$$

$$AS3=\{AS3(0),AS3(1),AS3(2),\ldots\} \quad \text{(Formula 1)}$$

The signal processing unit 111 averages three scans A corresponding to the same position on the X-axis to calculate one scan A. That is, a scan A AS(x) at a position x in the X-axis direction is calculated by the following (Formula 2).

$$AS(x)=(AS3(x-2)+AS2(x-1)+AS1(x))/3 \quad \text{(Formula 2)}$$

In this way, the scan A AS(x) is newly produced to configure a tomographic image, and the tomographic image is output to the display unit 5. Because the scan number of the scans A of the scan A AS(x) at x=0, 1 and x=W2−2, W2−1 is, however, insufficient, the scan A AS(x) is calculated on the basis of substantially one or two scans A.

In addition, the tomographic image produced in the step of S400 will be referred to as a watching tomographic image in the following description. Because three scans A are averaged as above, random noise is suppressed, and the S/N ratio or the resolution of the watching tomographic image is improved in comparison with the wide area tomographic image acquired in the step of S100, and the watching tomographic image becomes a tomographic image suitable for more minute observation. Furthermore, if the sampling interval of the interference signals is set to be shorter than that in the step of S100 in the present step, it is also possible to acquire a tomographic image having higher resolution.

Figure 6B:
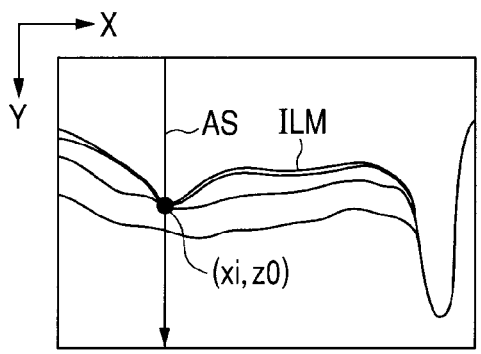
Figure 6C:
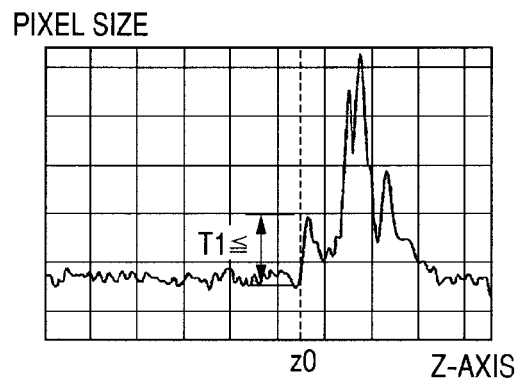
Figure 6D:
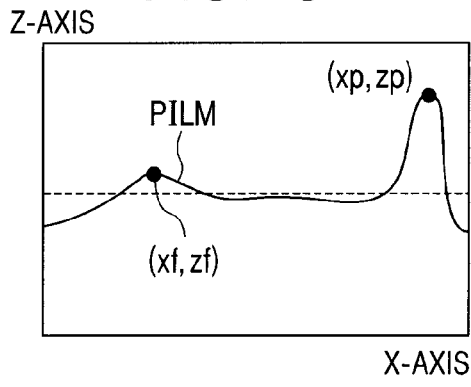
Figure 6E:
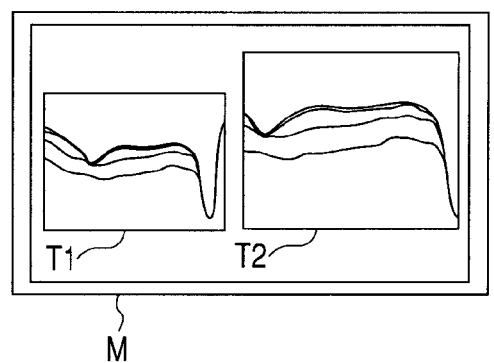

Next, in the step of S500, which is a display step, a tomographic image is displayed as follows. The display unit 5 arranges two tomographic images input from the acquiring unit 1 to display them. FIG. 6E illustrates the form of the display. In the same figure, the display unit 5 is a liquid crystal monitor M, and the display unit 5 displays a wide area tomographic image T1 and a watching tomographic image T2 side-by-side. Thereby, it is possible to observe a minute tomographic image of a region more important for diagnosis while observing the state of a wide range retina.

Figure 5A:
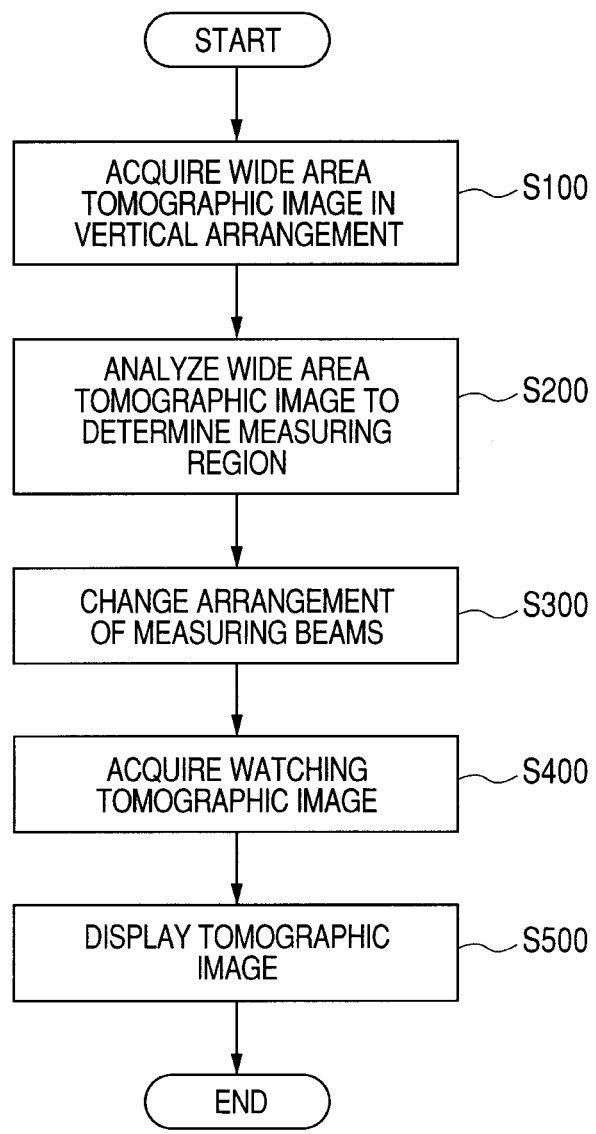
FIGS. 5A and 5B are flow charts for illustrating the operation of the imaging apparatus in the first embodiment of the present invention.
Figure 5B:
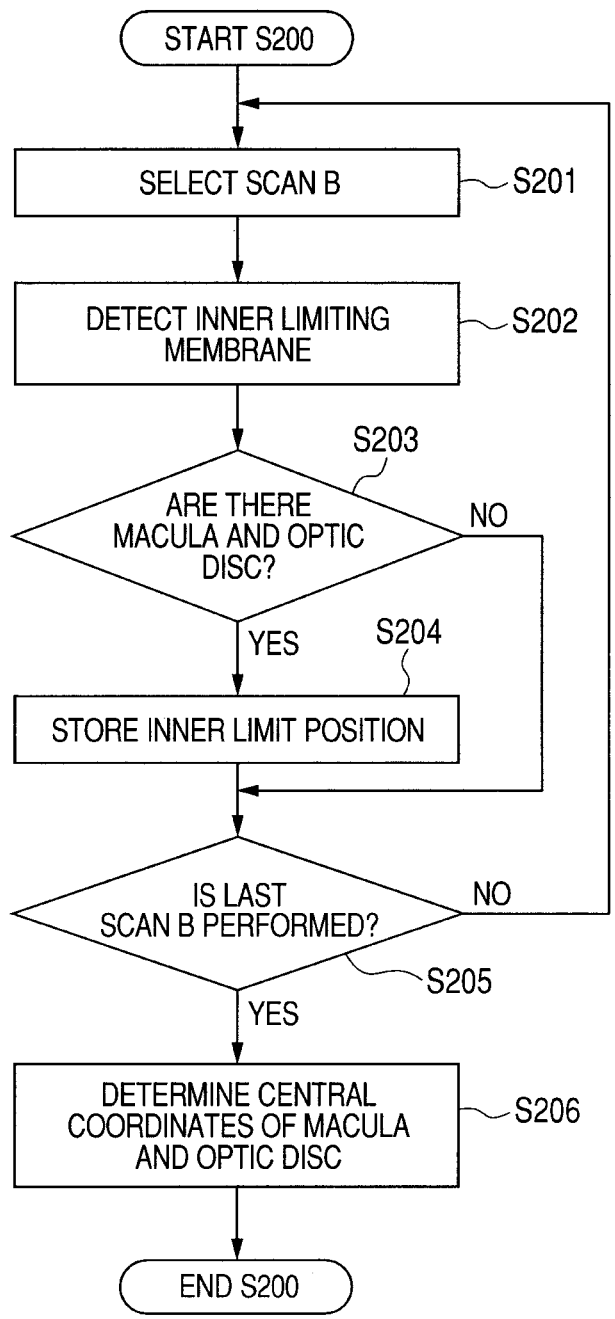

Next, the minute operation of the analyzing unit 3 in the step of S200 is described with further reference to the flow chart of FIG. 5B.

First, in the step of S201, the scan B is selected as follows. The analyzing unit 3 selects one scan B from the input wide area tomographic image as an analysis object. For this, it is only necessary to select, for example, the tomographic images illustrated in FIG. 3B in ascending order of the Y-coordinates.

Next, in the step of S202, the analyzing unit 3 detects an inner limiting membrane from the selected scan B. The inner limiting membrane is a layer contacting with the vitreous body in the retina layer, and is the part denoted by ILM in FIG. 6B. First, the analyzing unit 3 applies a low pass filter to the scan B, and, next, acquires the position of a pixel at which the difference between adjoining pixels is equal to or more than a threshold T1 and the Z-coordinate is the smallest in the Z-axis direction to each scan A constituting the scan B after the processing. That is, if the profile of the pixel values of the scan A AS in FIG. 6B is the one illustrated in FIG. 6C, the analyzing unit 3 detects z0, the minimum z-coordinate among those at which the differences between adjoining pixel values exceed T1. An appropriate value for detecting the inner limiting membrane is selected from a plurality of tomographic images as the threshold T1 beforehand to be stored in a not-illustrated memory in the analyzing unit 3 here. This process is performed to all the scans A constituting the scan B. Because the number of pixels of the wide area tomographic images in the X-axis direction is W1, W1 coordinate values PILM in the Z-axis direction, which are expressed by the following (Formula 3) are acquired to each scan B as a result.

$$PILM=\{z0,z1,z2,\ldots,zw1-1\} \quad \text{(Formula 3)}$$

Next, in the step of S203, the analyzing unit 3 detects whether the macula MF and the optic disc OP exist in the scan B that is the object now or not from the coordinate values PILM in the Z-axis direction. To put it concretely, as illustrated in FIG. 6D, the analyzing unit 3 detects two peaks (xf, zf) and (xp, zp) of the coordinate values PILM in the Z-axis direction corresponding to the macula MF and the optic disc OP, respectively. If the two peaks are not detected here, the process of the analyzing unit 3 moves to the step of S205. If the two peaks are detected, the process of the analyzing unit 3 moves to the step of S204.

Next, in the step of S204, the inner limit position is stored as follows. The analyzing unit 3 stores the two peak coordinates (xf, zf) and (xp, zp), detected at the step of S203, in the not-illustrated memory in the analyzing unit 3 together with the coordinate value in the Y-axis direction of the scan B in which the peak coordinates (Xf, zf) and (xp, zp) have been detected.

Next, in the step of S205, the last scan B is performed as follows. The analyzing unit 3 determines whether the scan B, which is now set as the object, is the last scan B of the wide area tomographic images or not. If it is true, the process is moved to the step of S206. If it is not true, the process is moved to the step of S201.

In the step of S206, the central coordinates of the macula MF and the optic disc OP are determined as follows. The analyzing unit 3 detects the center position of the macula MF and the optic disc OP from the peak values stored in the step of S204. To put it concretely, for example, if it is supposed that the data corresponding to the peak value corresponding to the stored macula MF is (xf_max, zf_max), then the coordinate value in the X-axis direction of the macula MF is set to xf_max, and the coordinate value in the Y-axis direction is set to the coordinate value in the Y-axis direction of the scan B in which the peak value has been detected. That is, if the coordinate value in the Y-axis direction of the scan B is set to yf, then the coordinates of the center CMF of the macula MF become (xf_max, yf). Similar processing is performed to the optic disc OP, and the position of the center COP is acquired.

Next, the analyzing unit 3 determines the measuring region R2 as a range as the result of addition of a certain offset to the CMF and the COP. This offset value may be stored in the imaging apparatus as a device parameter of the imaging apparatus as a value necessary at the time of imaging a normal object (subject). Alternatively, the operator of the apparatus may input the offset value with a not-illustrated user interface before imaging.

As described above, the imaging apparatus by the present embodiment can acquire a wide range tomographic image speedily by performing scanning with a plurality of measuring beams in the vertical arrangement. Then, by performing measurement of the watching region acquired by analyzing the tomographic image as an object by changing the measuring beams to the horizontal arrangement, by which a high S/N ratio or high resolution can be acquired, a tomographic image of a high image quality can be acquired while suppressing the increase of the measuring time. Hence, in the case of imaging a tomographic image having a high image quality in a part of the region of an image range, it is possible to image only the part relatively densely over time under the conditions set for enhancing the image quality thereof. As a result, it is possible to effectively image a watching region without lengthening the whole measuring time.

In addition, although the description has been provided on the premise of three measuring beams in the present embodiment, the present invention is not limited to this, but an arbitrary number of measuring lights, which are two or more, can be used. Furthermore, although the wide area tomographic image and the watching tomographic image are sev- erally once imaged in the present embodiment, the present invention is not limited to this. For example, the watching tomographic image may be imaged a plurality of times, and the scans A may be acquired more finely while gradually narrowing the measuring range.

Furthermore, although the present embodiment sets a fundus retina as an object and acquires a tomographic image especially effective for the diagnosis of glaucoma, the present invention is not limited to this. The present invention can realize an imaging apparatus capable of enhancing the speed of measurement overall and acquiring a tomographic image having a higher image quality in an important part not only to the measurement by the OCT used in the diagnosis of the other diseases of the fundus retina as an object, it is needless to say, but also to the measurement by the OCT used in the other medical departments and the fields other than medical service.

As another embodiment, the imaging method according to the embodiment may be stored in a computer-readable storage medium (such as, a flexible disc, a hard disc, an optical disc, a magneto-optical disc, a CD-ROM, a CD-R, a magnetic tape, a nonvolatile memory card, a ROM, an EEPROM, and a Blu-ray Disc) as a program for enabling a computer to execute the imaging method. Furthermore, as a still another embodiment, the present invention may be a program for enabling a computer to execute the imaging method.

Second Embodiment

Although the first embodiment is configured to display a wide area tomographic image and a watching tomographic image side-by-side as illustrated in FIG. 6E, the present invention is not limited to such a configuration. In the following, a mode of synthesizing a wide area tomographic image and a watching tomographic image together to display them will be described.

Figure 7A:
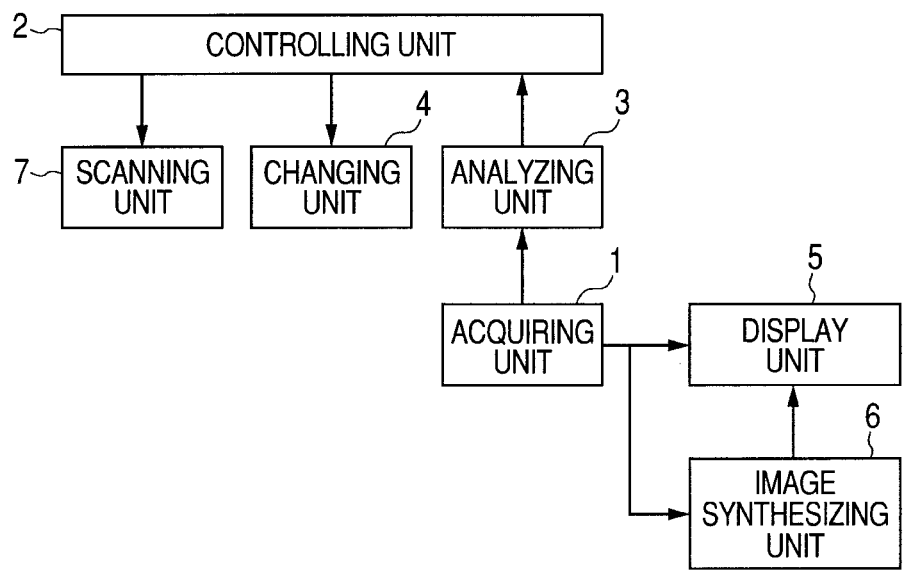
FIGS. 7A, 7B, 7C, and 7D are diagrams for illustrating the configuration of the imaging apparatus in a second embodiment of the present invention.
Figure 7B:
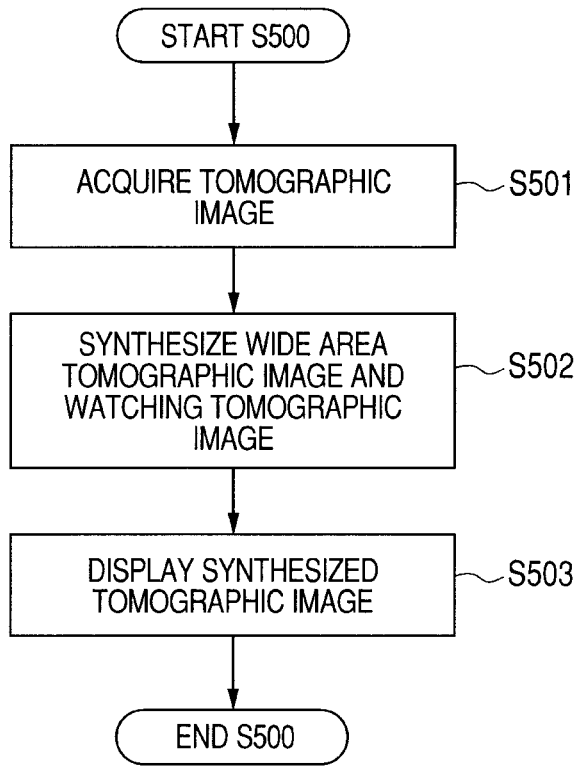

FIG. 7A illustrates the configuration of an imaging apparatus of the present embodiment. The configuration of FIG. 7A is the same as that of the first embodiment illustrated in FIG. 1A other than an added image synthesizing unit 6, and accordingly the descriptions of the overlapping parts will be omitted. The present embodiment will be described mainly about the operation of the display unit 5 and the image synthesizing unit 6 at the step of S500 with reference to the flow chart illustrated in FIG. 7B.

Figure 7C:
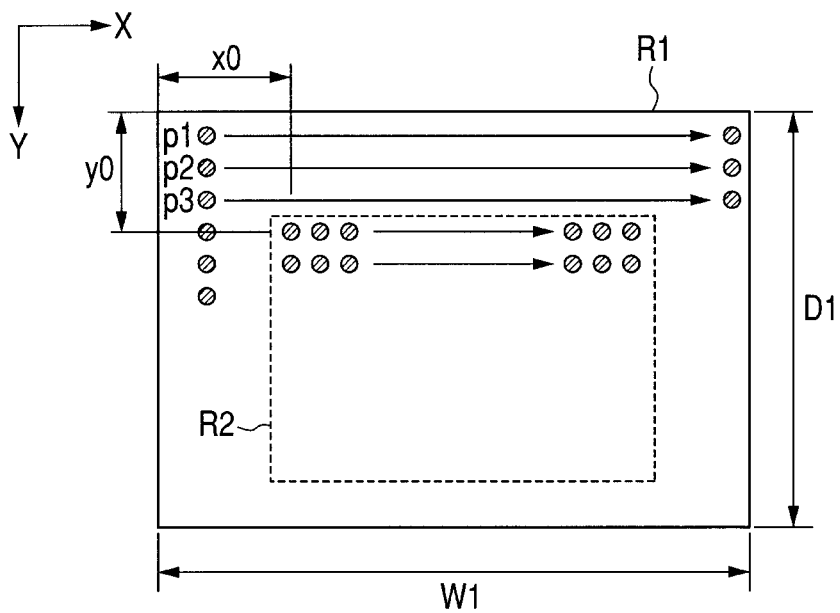

First, in the step of S501, a tomographic image is acquired as follows. The image synthesizing unit 6 receives the inputs of both of a wide area tomographic image and a watching tomographic image from the acquiring unit 1. Furthermore, the image synthesizing unit 6 receives an input of the offset coordinate values (x0, y0) of a watching tomographic image in the case of adopting the wide area tomographic image as a criterion from the acquiring unit 1. FIG. 7C illustrates the relation between the measuring region R1 of the wide area tomographic image expressed by the offset coordinate values and the measuring region R2 of the watching tomographic image. The offset coordinate values (x0, y0) can be calculated by the acquiring unit 1 when the analyzing unit 3 determines the measuring region R2 in S200 of the flow chart illustrated in FIG. 5A, and the offset coordinate values (x0, y0) are stored in the acquiring unit 1.

Next, in the step of S502, the image synthesizing unit 6 synthesizes the input wide area tomographic image and the watching tomographic image to one tomographic image. In addition, the synthesized tomographic image will be referred to as synthesized tomographic image in the subsequent description. The synthesis of the tomographic images is performed by substituting the pixels of the watching tomographic image for the pixels of the positions expressed by the offset coordinate values (x0, y0) in the wide area tomographic image as illustrated in FIG. 7C, and the produced synthesized tomographic image is output to the display unit 5.

Figure 7D:
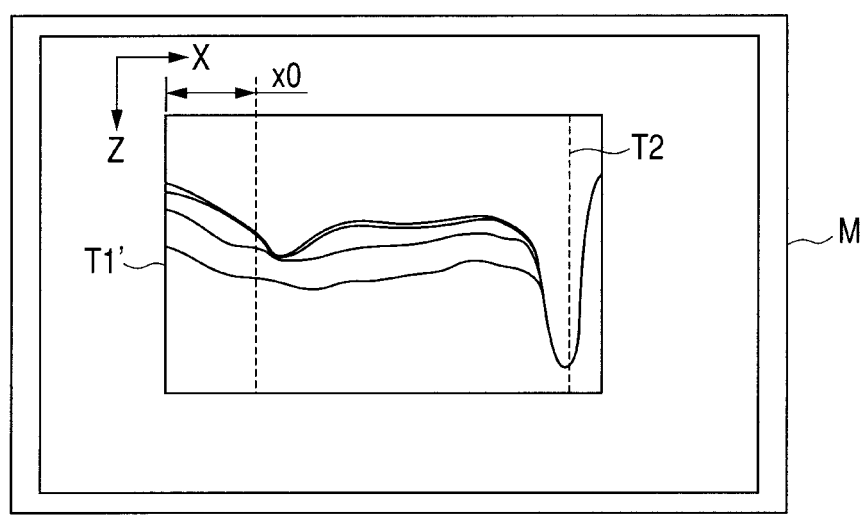

Next, in the step of S503, the synthesized tomographic image is displayed as follows. The display unit 5 displays the input synthesized tomographic image on a monitor M. FIG. 7D is an example of a display mode at this time, and one scan B in the synthesized tomographic image is displayed. In FIG. 7D, T1' is a synthesized tomographic image, and a corresponding region is replaced with the data of the watching tomographic image T2 as illustrated by broken lines.

In this way, by substituting the tomographic image produced by the scanning in the horizontal arrangement with the measuring beams for a part of the tomographic image acquired by scanning at a high speed in the vertical arrangement with the measuring beams in the first, a wide measuring region is covered, and a tomographic image having a higher image quality can also be displayed in a necessary part.

In addition, although the scan B image of the synthesized tomographic image T1' is displayed as a two-dimensional image in the aforesaid display mode, the present invention is not limited to this, but the synthesized tomographic image T1' may three-dimensionally be displayed by volume rendering.

Furthermore, in the display mode illustrated in FIG. 7D, boundary lines may be displayed by being superimposed on the tomographic image in order to be able to sight the boundaries of the watching tomographic image. For example, by displaying the boundary parts with the broken lines as illustrated in FIG. 7D, an observer can easily discern the part due to the watching tomographic image.

Third Embodiment

The aforesaid embodiments are severally configured to change the scanning direction thereof from the vertical arrangement of the measuring beams to the horizontal arrangement of them at the time of acquiring two tomographic images, but the present invention is not limited to such a configuration. In the following, a third embodiment of setting the arrangement of the measuring beams thereof only to the horizontal arrangement, and of substantially changing the distances between the measuring beams will be described.

In the present embodiment, because the configuration and the basic flow of operation of the imaging apparatus are the same as those of FIGS. 1A and 5A, the descriptions of the overlapped parts are omitted. The content of the steps of S300 and S400, which is the characteristic part of the present embodiment, is minutely described in the following.

First, in the step of S300, the intervals between the measuring beams are changed as follows. Similarly to the first embodiment, when the controlling unit 2 receives the inputs of the position and the number of pixels of the measuring region R2 from the analyzing unit 3, the controlling unit 2 outputs a command of changing the intervals between the three measuring beams to the changing unit 4. The changing unit 4 changes the arrangement so that the intervals between the three measuring beams on the fundus retina, which is the object to be measured, become relatively narrower in comparison with those at the step of S100 in response to the command. To put it concretely, the changing unit 4 changes the arrangement so that the lengths of the measuring beam intervals d, illustrated in FIG. 8A, become relatively smaller on the retina. This may be realized by mechanically changing the distances between the three optical fibers, but the present embodiment realizes it by controlling the speeds of the measuring beams in main scanning not by physically changing the intervals between the actual measuring beams.

Next, in the step of S400, a watching tomographic image is acquired as follows. First, the changing unit 4 outputs a signal for changing the speed of the main scanning to the scanner controlling unit 105 in the acquiring unit 1. Next, the scanning unit 7 is controlled so as to change the speed of the main scanning by the scanner controlling unit 105. Then, the acquiring unit 1 acquires a watching tomographic image having a high image quality. FIG. 8B is a diagram illustrating the loci of the measuring beams in the scanning in the present embodiment. In FIG. 8B, broken lines express the loci of the respective measuring beams at the time of acquiring a wide area tomographic image in the step of S100, and on the other hand, solid lines express the loci of a watching tomographic image acquired in the step of S400. As illustrated in FIG. 8B, each measuring beam moves by $2\Delta x$ in one sampling period at the time of acquiring the wide area tomographic image, and on the other hand, each measurement ling moves by $\Delta x$ at the time of acquiring the watching tomographic image. Consequently, the intervals between the respective measuring beams substantially become double on the retina, and the sample number of the wide area tomographic image in the X-axis direction becomes a half, but the tomographic image can be acquired for a half time.

In addition, because the number of pixels of the wide area tomographic image in the X-axis direction becomes half in the present embodiment, as illustrated in the second embodiment, the up-sampling of the wide area tomographic image is performed in the X-axis direction before the synthesis of the tomographic image, and an interpolation is performed. Only the thing required for the interpolation is to use a publicly known technique, such as the nearest neighbor interpolation or the spline interpolation.

As described above, according to the present embodiment, the imaging apparatus by the present invention can be realized with a simple configuration without mechanically changing the arrangement of the measuring beams. Furthermore, because the horizontal arrangement is used even at the time of acquiring the wide area tomographic image, the S/N ratio of the imaging apparatus or the resolution thereof can be improved by averaging the three scans A.

Fourth Embodiment

In each of the aforesaid embodiments, the analyzing unit 3 is configured to determine the measuring region of the watching tomographic image by analyzing the wide area tomographic image, but the present invention is not limited to such a configuration. In the following, the method of determining a measuring region of the watching tomographic image on the basis of the imaging information pertaining to the past same object (subject) will be described.

The configuration of the imaging apparatus by the present embodiment is the same as that of FIG. 1A, but the configuration is different from that of FIG. 1A in that the analyzing unit 3 has the function of inputting the past imaging information pertaining to the same object (subject). To put it concretely, the imaging information corresponds to a part regarded as the region to be watched in the past imaging. That is, as described above, in the case where the imaging apparatus is an ophthalmologic imaging apparatus, the past diagnostic information of the same patient is read as the imaging information by the analyzing unit 3. The diagnostic information is the information pertaining to a lesion area, which has been diagnosed in a past examination. To put it concretely, for example, the measuring region R2 of the watching tomographic image acquired in FIGS. 6A to 6E is saved as past diagnostic information, and the analyzing unit 3 can read the measuring region R2 through a diagnostic information acquiring unit 303 in FIG. 1C.

Figure 9A:
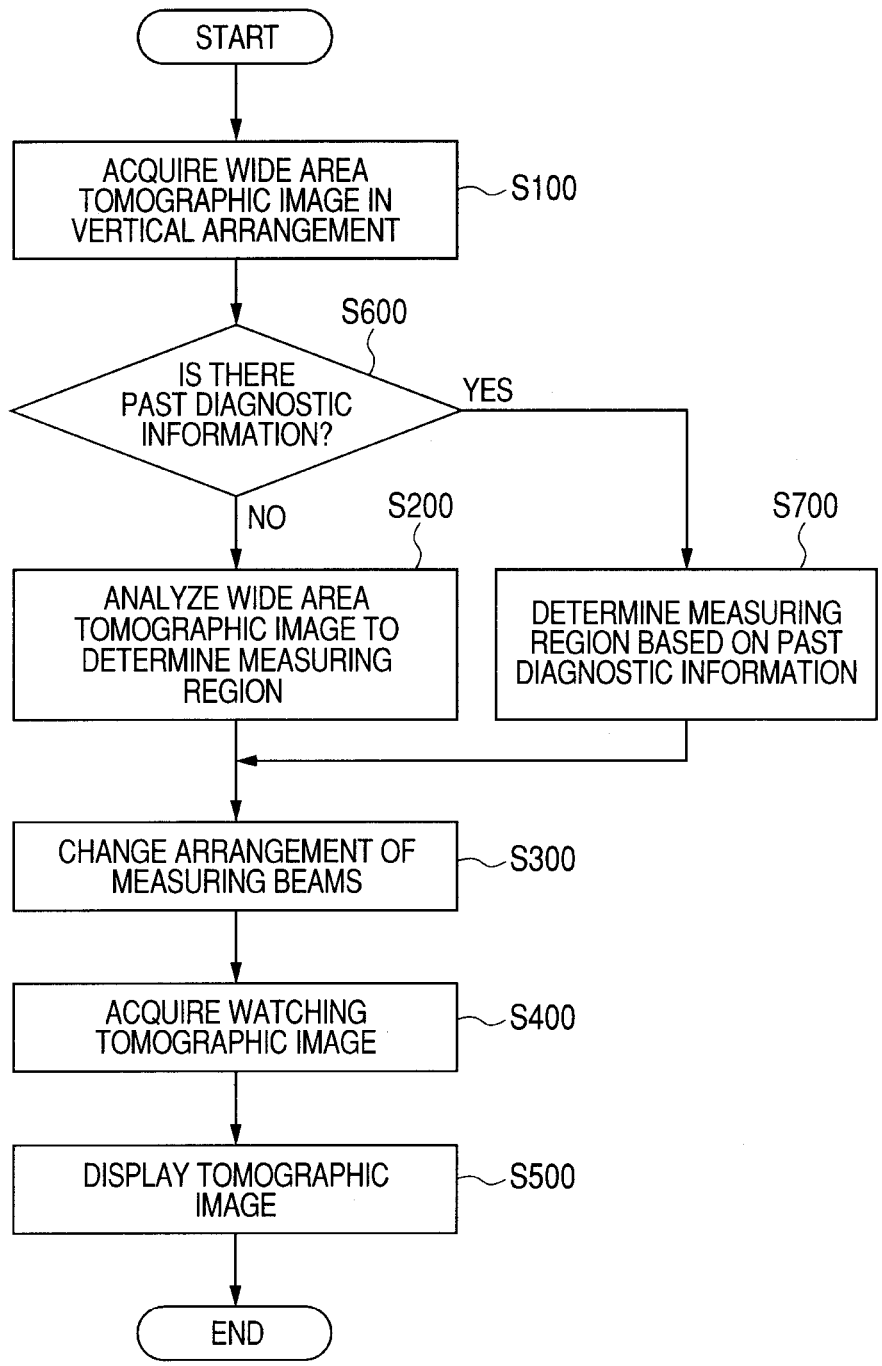
FIGS. 9A and 9B are flow charts for illustrating the operation of the imaging apparatus of each embodiment of the present invention.

FIG. 9A is a flow chart illustrating the operation of the imaging apparatus in the present embodiment. In FIG. 9A, the same processing parts as those of the flow chart of each of the aforesaid embodiments are denoted by the same marks as those of the aforesaid embodiments, and the flow chart is different from those of the aforesaid embodiments in that the steps of S600 and S700 are added. Accordingly, the descriptions of the same parts are omitted, and the added parts will be described in the following.

In the step of S600, it is checked as follows whether any past diagnostic information exists or not. At this time, the analyzing unit 3 checks whether the diagnostic information pertaining to the same object (subject) exists or not after the completion of the acquisition of the wide area tomographic image in the step of S100. It is only necessary for performing this to retrieve the tomographic image having the ID number same as the one peculiar to each patient, which is an object (subject). It is supposed that the diagnostic information is saved in a not-illustrated storage apparatus of the imaging apparatus illustrated in FIG. 1A, and that the ID number of the patient of the present measuring object is read into the analyzing unit 3 with a not-illustrated user interface before imaging. If the past diagnostic information exists here, the process moves to the step of S700. If the past diagnostic information does not exist, the process moves to the step of S200.

In the step of S700, a measuring region is determined from the past diagnostic information as follows. The analyzing unit 3 determines the measuring region R2 stored as the past diagnostic information as a new measuring region as described above. In addition, although the measuring region R2 of the watching tomographic image is supposed to be saved as the past diagnostic information in the above description, the past diagnostic information is not limited to this, but the past diagnostic information may be the region saved as a lesion area in a past diagnosis.

By configuring the imaging apparatus in this way, it is possible to change the arrangement of the measuring beams in a region to be especially watched in diagnosis to acquire a tomographic image having a higher image quality.

Fifth Embodiment

Although the imaging apparatus of each of the aforesaid embodiments is configured to determine the measuring region of a watching tomographic image from a wide area tomographic image or past diagnostic information, to change the arrangement of measuring beams, and to acquire a watching tomographic image, the present invention is not limited to such a configuration. In the following, the analyzing unit of the present embodiment analyzes whether an abnormal structure of a subject is included in a tomographic image or not. Furthermore, the controlling unit according to the present embodiment is configured to be able to determine whether to acquire a tomographic image again or not according to the existence of the abnormal structure.

Figure 9B:
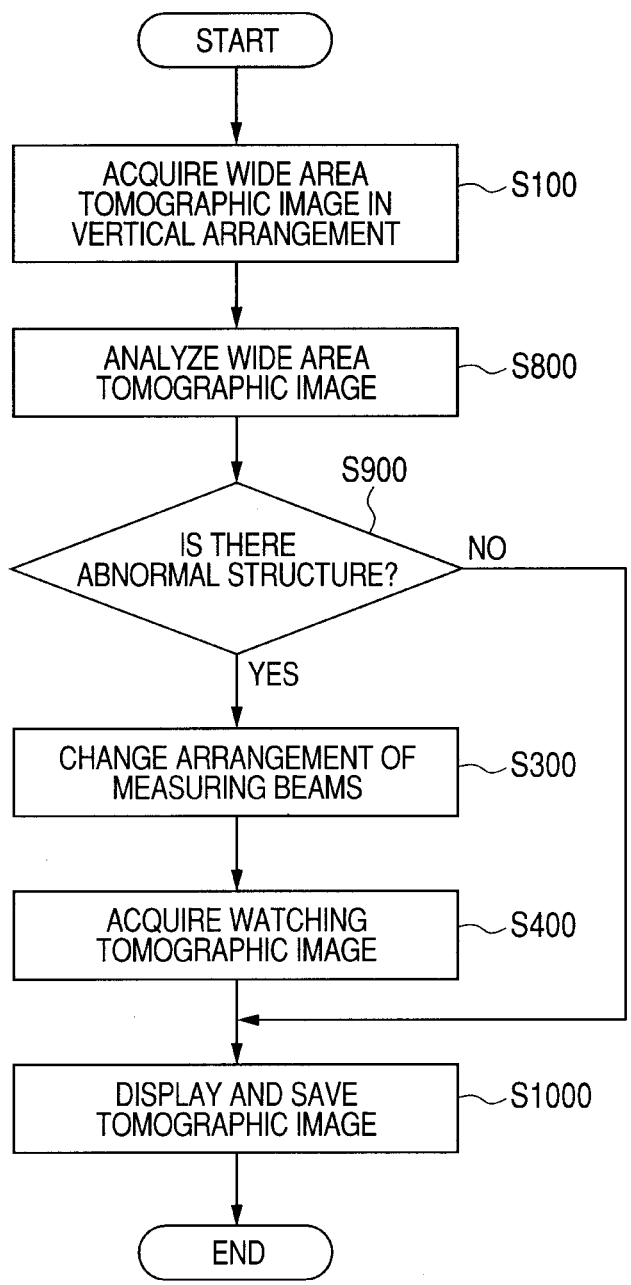

FIG. 9B is a flow chart illustrating the operation of the imaging apparatus in the present embodiment. In FIG. 9B, the parts performing the same operation as that of the aforesaid ones are omitted to be described, and the parts peculiar to the present embodiment will be described in the following.

In the step of S800, a wide area tomographic image is analyzed as follows. At this time, the analyzing unit 3 analyzes the wide area tomographic image to detect whether a structure different from normal ones is included or not. For example, if a leucoma L exists on a fundus as illustrated in FIG. 8C, the pixel values in the region of the leucoma L become larger than those in the other regions. This is because the reflectance in the leucoma L is higher than those in the other regions of the fundus. As a result, the analyzing unit 3 analyzes each of the scans A constituting the scan B to examine the existence of the parts in which the pixel values exceed those in the regions of normal structures greatly, thereby determining the existence of the leucoma L. In addition, the leucoma is a swelling (soft leucoma) of a part of a nerve fiber on a retina or a clot of constituent parts of the blood (hard leucoma) in a blood vessel on the retina.

To put it concretely, first, the existence of a pixel exceeding a predetermined threshold TL is examined. Next, the continuity of the pixels exceeding the predetermined threshold TL is examined. Then, the number of continuous pixels is counted. Furthermore, if the counted number of pixels is equal to or more than a predetermined number, it is determined that an abnormal structure, such as the leucoma L, exists. If it is determined that the abnormal structure exists at the step of S900, the process advances to the step of S300. If it is determined that the abnormal structure does not exist, the process advances to the step of S1000.

In the step of S1000, a tomographic image is displayed and saved as follows. Although the step of S1000 is basically similar to the step of S500, the step of S900 is different from the step of S500 in displaying only the wide area tomographic image if it is determined that there are no abnormal structures at the step of S900. Furthermore, the displayed tomographic image is saved in a not-illustrated storage apparatus, such as a storage medium of a hard disc, an MO, and the like, as a file. FIG. 8D illustrates the format of the saved file. This file includes the ID number capable of specifying a patient, the information such as the date and time of imaging, an analysis result in the step of S800, and tomographic image data. If it is determined that there are no abnormal structures from the analysis result, only a wide area tomographic image is included in the part of the tomographic image data. If it is determined that there are one or more abnormal structures, the data of a wide area tomographic image and a watching tomographic image is included.

As described above, according to the present embodiment, only in the case where there are one or more abnormal structures by the analysis of a wide area tomographic image, the arrangement of measuring beams is changed to enable the acquisition of a watching tomographic image. Consequently, even if almost all imaging objects are normal as in the case of health screening and the necessity of acquiring a watching tomographic image does not exist in all cases, effective imaging can be performed.

Sixth Embodiment

Although the changing unit 4 changes the arrangement of the measuring beams from the vertical arrangement to the horizontal arrangement by turning the optical fibers in the aforesaid first embodiment, the present invention is not limited to such a configuration. In the following, the mode of acquiring a wide area tomographic image and a watching tomographic image without mechanically turning the optical fibers will be described. In addition, because the present embodiment is different from the embodiment of FIG. 5A in the method of changing the arrangement of the measuring beams in the step of S300, the description will mainly be given to this part, and the minute descriptions of the other parts will be omitted.

FIGS. 10A to 10F illustrate the arrangements of the measuring beams of the scanning optical system 104 in the present embodiment, and five optical fibers are provided in total. It is enabled to select three of the five optical fibers to radiate measuring beams. Accordingly, it is supposed that the beam splitter 102 illustrated in FIG. 1B splits the outputs of the SLD 101 into five in the present embodiment. Furthermore, not-illustrated shutter mechanisms are provided between the beam splitter 102 and the fiber coupler 103, to enable the changing of the arrangement of the measuring beams entering an eye to be inspected.

Figure 10A:
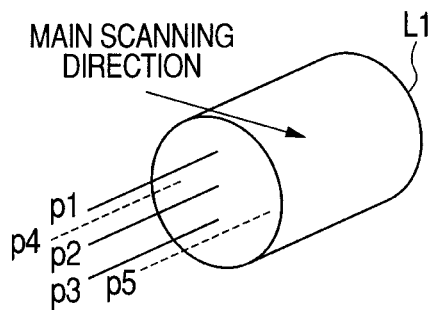
FIGS. 10A, 10B, 10C, 10D, 10E, and 10F are views for illustrating the arrangements of the measuring beams in a sixth embodiment of the present invention.
Figure 10B:
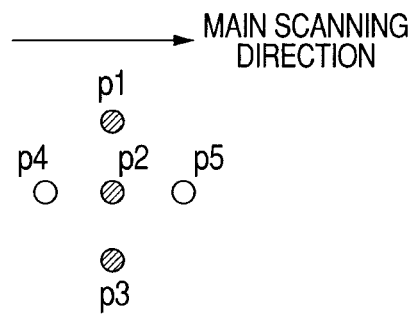
Figure 10C:
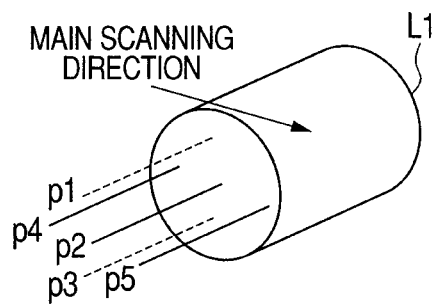
Figure 10D:
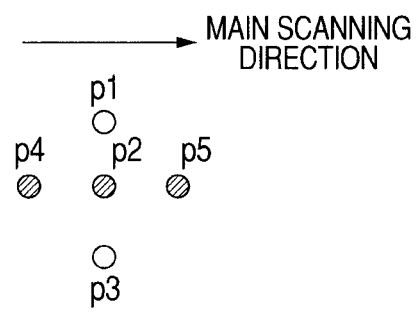

The imaging apparatus by the present invention forms measuring beam fluxes in the vertical arrangement by blocking out p4 and p5 with the shutters as illustrated in FIG. 10A in the step of S100 for acquiring a wide area tomographic image on the basis of such a configuration. In the step of S200, the wide area tomographic image is analyzed to determine a measuring region of a watching tomographic image. After that, by blocking out p1 and p3 and opening p4 and p5 as illustrated in FIG. 10D when the arrangement of the measuring beams is changed at the step of S300, the measuring beam fluxes of the horizontal arrangement can be formed as illustrated in the FIG. 10C. Because the subsequent process is similar to that of the first embodiment, the description thereof is omitted.

Figure 10E:
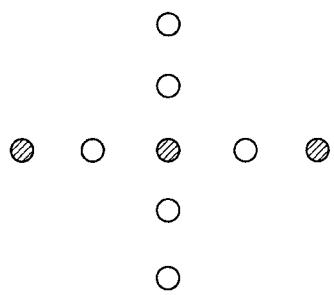
Figure 10F:
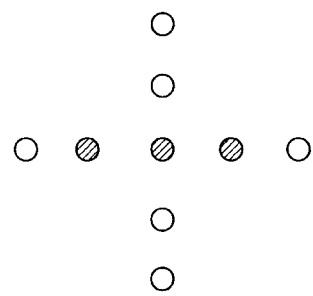

Furthermore, as described in the third embodiment, when the intervals between the measuring beams arranged in the horizontal direction are changed, for example, it is only necessary to control the shutters so as to change the intervals of the measuring beams arranged in the horizontal direction as FIG. 10E or 10F. That is, the measuring beam fluxes can be formed by selecting the measuring beams as illustrated in FIG. 10E when a wide area tomographic image is acquired or as illustrated in FIG. 10F when a watching tomographic image is acquired.

As described above, similar effects can be acquired by changing the radiation pattern of a plurality of measuring beams without turning the optical fibers in the present invention. In addition, it is needless to say that the number of the measuring beams to be radiated is not limited to those in FIGS. 10A to 10F in the present invention.

Other Embodiments

The present invention is not limited to the aforesaid modes, but can be realized in various modes.

The imaging apparatus illustrated in FIG. 1A can be realized by hardware or a combination of hardware and software. In this case, each section in FIG. 1A other than the acquiring unit 1 corresponds to a circuit or an ASIC for realizing a specific function in the case of hardware, or a module in the case of software. Furthermore, if all of the components are realized by software, the software can be made to be a module operating on a general purpose PC.

Furthermore, although the storage apparatus of the tomographic images has been described to be in the imaging apparatus in the fifth embodiment, the storage apparatus can be configured as an image server connected to the imaging apparatus through a network.

Furthermore, it is also possible to configure the imaging apparatus in such a way that the acquiring unit 1 is connected to the other components through a network, and that the other components is realized as software operating on a general purpose PC.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2009-123908, filed May 22, 2009, and No. 2010-068281, filed Mar. 24, 2010 which are hereby incorporated by reference herein in their entirety.

The invention claimed is:

1. An imaging apparatus, comprising:
    an irradiating unit configured to irradiate an object with a plurality of measuring beams;
    a changing unit configured to change the positional relation among irradiation positions of the plurality of measuring beams irradiating a predetermined layer of the object by the irradiating unit;
    a scanning unit configured to scan the plurality of measuring beams in the positional relation changed by the changing unit; and
    an acquiring unit configured to acquire an optical coherence tomographic image of the object based on the plurality of measuring beams used for the scanning by the scanning unit.

2. The imaging apparatus according to claim 1, wherein the object is an eye to be inspected, and
    the changing unit is means for changing intervals among the irradiation positions of the plurality of measuring beams on a fundus surface of the eye to be inspected.

3. The imaging apparatus according to claim 1, wherein the changing unit changes a width of the irradiation positions in a scanning direction.

4. The imaging apparatus according to claim 1, wherein the changing unit is means for changing an arrangement of the irradiation positions of the plurality of measuring beams from a main scanning direction to a sub scanning direction of the scanning unit or means for changing the arrangement of the irradiation positions of the plurality of measuring beams from the sub scanning direction to the main scanning direction.

5. The imaging apparatus according to claim 1, further comprising a plurality of fiber ends configured to emit the plurality of measuring beams to the object, wherein the changing unit is means for rotating the plurality of fiber ends around an emitting direction of the plurality of measuring beams serving as an axis around which the plurality of fiber ends rotate or means for selecting some of the plurality of fiber ends.

6. The imaging apparatus according to claim 1, further comprising:
    an analyzing unit configured to analyze a wide area image of the object acquired in a scanning region wider than that for acquiring the optical coherence tomographic image; and
    a controlling unit configured to control the changing unit by using an analysis result of the analyzing unit.

7. The imaging apparatus according to claim 1, wherein the changing unit changes a width of the irradiation positions in a sub scanning direction.

8. An imaging apparatus, comprising:
an irradiating unit configured to irradiate an object with a plurality of measuring beams;
a changing unit configured to change a positional relation among irradiation positions of the plurality of measuring beams irradiating the object by the irradiating unit;
a scanning unit configured to scan the plurality of measuring beams in the positional relation changed by the changing unit;
an acquiring unit configured to acquire an optical coherence tomographic image of the object based on the plurality of measuring beams used for the scanning by the scanning unit;
an analyzing unit configured to analyze a wide area image of the object acquired in a scanning region wider than that for acquiring the optical coherence tomographic image; and
a controlling unit configured to control the changing unit by using an analysis result of the analyzing unit.

9. The imaging apparatus according to claim 8, wherein
the analyzing unit determines a watching region of the object from the wide area image;
the changing unit changes the positional relation in such a way that intervals among the irradiation positions of the plurality of measuring beams are narrower than those at the time of acquiring the wide area image; and
the acquiring unit acquires the optical coherence tomographic image in the watching region in the positional relation changed by the changing unit.

10. The imaging apparatus according to claim 8, wherein
the object is an eye to be inspected, and
the changing unit is means for changing intervals among the irradiation positions of the plurality of measuring beams on a fundus surface of the eye to be inspected.

11. The imaging apparatus according to claim 8, wherein the changing unit changes a width of the irradiation positions in a scanning direction.

12. The imaging apparatus according to claim 8, wherein the changing unit changes a width of the irradiation positions in a sub scanning direction.

13. An imaging method, comprising the steps of:
irradiating an object with a plurality of measuring beams;
scanning the plurality of measuring beams;
acquiring an optical coherence tomographic image of the object based on the plurality of measuring beams;
analyzing a wide area image of the object acquired in a scanning region wider than that for acquiring the optical coherence tomographic image; and
changing a positional relation among irradiation positions of the plurality of measuring beams irradiating the object by using an analysis result of the analyzing step.

14. The imaging method according to claim 13, wherein
the object is an eye to be inspected;
the step of changing is the step of changing intervals among the irradiation positions of the plurality of measuring beams on a fundus surface of the eye to be inspected.

15. The imaging method according to claim 13, further comprising the step of determining a watching region of the object from the wide area image, wherein
the changing step changes intervals among the irradiation positions of the plurality of measuring beams to be narrower than those for acquiring the wide area image; and
the acquiring step acquires the tomographic image in the watching region in the changed positional relation.

16. A program for enabling a computer to execute the imaging method according to claim 13.

17. An imaging apparatus, comprising:
an irradiating unit configured to irradiate an object with a plurality of measuring beams;
a scanning unit configured to align irradiation positions of the plurality of measuring beams, irradiating a predetermined layer of the object by the irradiating unit, in a main scanning direction to scan the plurality of measuring beams;
a changing unit configured to change the scanning speed of the plurality of measuring beams in the main scanning direction; and
an acquiring unit configured to acquire an optical coherence tomographic image of the object based on the plurality of measuring beams used for the scanning by the scanning unit.

18. The imaging apparatus according to claim 17, wherein
the object is an eye to be inspected, and
the changing unit is means for changing intervals among the irradiation positions of the plurality of measuring beams on a fundus surface of the eye to be inspected.

19. The imaging apparatus according to claim 17, wherein the changing unit changes a width of the irradiation positions in a scanning direction.

20. The imaging apparatus according to claim 17, wherein the changing unit changes a width of the irradiation positions in a sub scanning direction.

21. An imaging method comprising:
an irradiating step of irradiating an object with a plurality of measuring beams;
a changing step of changing the positional relation among irradiation positions of the plurality of measuring beams irradiating a predetermined layer of the object by the irradiating step;
a scanning step of scanning the plurality of measuring beams in the positional relation changed by the changing step; and
an acquiring step of acquiring an optical coherence tomographic image of the object based on the plurality of measuring beams used for the scanning by the scanning step.

22. A non-transitory computer-readable storage medium storing a computer program instructing a computer to execute the method of claim 21.

23. An imaging method comprising:
an irradiating step of irradiating an object with a plurality of measuring beams;
a scanning step of aligning irradiation positions of the plurality of measuring beams, irradiating a predetermined layer of the object by the irradiating step, in a main scanning direction to scan the plurality of measuring beams;
a changing step of changing the scanning speed of the plurality of measuring beams in the main scanning direction; and
an acquiring step of acquiring an optical coherence tomographic image of the object based on the plurality of measuring beams used for the scanning by the scanning step.

24. A non-transitory computer-readable storage medium storing a computer program instructing a computer to execute the method of claim 23.

25. An imaging apparatus comprising:
an irradiating unit configured to irradiate an object with a plurality of measuring beams;

a scanning unit configured to scan the object with the plurality of measuring beams;

an acquiring unit configured to acquire an optical coherence tomographic image of the object based on the plurality of scanned measuring beams;

a changing unit configured to change at least an interval among irradiation positions of the plurality of measuring beams in a scanning direction of the scanning unit;

an analyzing unit configured to analyze a wide area image of the object acquired in a scanning region wider than that for acquiring the optical coherence tomographic image; and a controlling unit configured to control the changing unit, by using an analysis result of the analyzing unit, in such a way that the interval at the time of acquiring the optical coherence tomographic image is narrower than that at the time of acquiring the wide area image.

26. An imaging method comprising the steps of:

acquiring an optical coherence tomographic image of an object based on a plurality of measuring beams;

analyzing a wide area image of the object acquired in a scanning region wider than that for acquiring the optical coherence tomographic image; and controlling a changing unit to change at least an interval among irradiation positions of the plurality of measuring beams in a scanning direction of a scanning unit, by using an analysis result of the analyzing step, in such a way that the interval at the time of acquiring the optical coherence tomographic image is narrower than that at the time of acquiring the wide area image.

27. A non-transitory computer-readable storage medium storing a computer program instructing a computer to execute the method of claim 26.

* * * * *